United States Patent [19]
Paul

[11] Patent Number: 5,733,262
[45] Date of Patent: Mar. 31, 1998

[54] BLOOD VESSEL CANNULATION DEVICE

[76] Inventor: Kamaljit S. Paul, 3220 Old Orchard La., Oshkosh, Wis. 54901

[21] Appl. No.: 634,564

[22] Filed: Apr. 18, 1996

[51] Int. Cl.⁶ .................................................. A61M 5/00
[52] U.S. Cl. ................... 604/116; 604/174; 128/DIG. 26
[58] Field of Search ........................... 604/174, 179, 604/180, 116; 128/DIG. 26

[56] References Cited

U.S. PATENT DOCUMENTS

| | | | |
|---|---|---|---|
| 2,402,306 | 6/1946 | Turkel | 604/174 |
| 3,210,816 | 10/1965 | Clemons | 128/DIG. 26 |
| 4,212,297 | 7/1980 | Johnson, Jr. | 604/174 |
| 4,883,053 | 11/1989 | Simon | 604/116 |
| 4,898,178 | 2/1990 | Wedel | 604/116 |
| 4,955,864 | 9/1990 | Hajduch | 604/174 |
| 5,167,630 | 12/1992 | Paul | 604/179 |

*Primary Examiner*—Sam Rimmell
*Assistant Examiner*—Luke J. Yen

*Attorney, Agent, or Firm*—Wilhelm Law Services S.C.

[57] ABSTRACT

This invention pertains to blood vessel cannulation devices and methods for sensing the location of a blood vessel, for cannulation with precision and ease. In preferred embodiments, the blood vessel cannulation device preferably comprises a mounting assembly for securing the device to a patient in the vicinity of a blood vessel. A rotating assembly is mounted to the mounting assembly for rotation with respect to the mounting assembly. A guide housing is mounted to the rotating assembly for traverse across the rotating assembly, and for rotating with the rotating assembly. Sensor guides in the guide housing receive one or more sensors which sense the blood vessel. Rotating the rotating assembly, and traversing the guide housing, enable bringing the bottom ends of the sensor guides into alignment with the blood vessel, correspondingly also bringing a cannula guide, also present in the guide housing, into alignment with the blood vessel. Thus, positioning of the cannula guide over the blood vessel to ensure precise cannulation, is assured by alignment of the bottom end of the cannula guide with respective bottom ends of the sensor guides.

16 Claims, 3 Drawing Sheets

BLOOD VESSEL CANNULATION DEVICE

FIELD OF THE INVENTION

This invention relates to devices and methods for sensing the location of a blood vessel.

BACKGROUND OF THE INVENTION

This invention pertains specifically to locating a blood vessel of a patient for cannulation, whereby a cannula is subsequently inserted into the blood vessel for purposes of adding substances (e.g. medicine), removing substances (e.g. blood samples), monitoring the patient (e.g. blood pressure), or the like.

The procedure of locating a blood vessel for venipuncture is difficult under certain conditions, including where the patient is in hypotension, where the blood vessel is not close to the skin due to patient obesity or other factors, where the blood vessel tends to displace during cannulation due to factors such as thickening of the wall of the blood vessel, or the like.

When locating a blood vessel for cannulation, it is desirable to accurately sense the location of the blood vessel through non-invasive means. Due to normal blood vessel curvature, it may be difficult to accurately place a cannula if only one point on the blood vessel is located. It is thus desirable to locate the blood vessel, account for orientation of the blood vessel, and insert the cannula adjacent the location point or points to reduce the possibility of missing the blood vessel.

It is an object of this invention to provide a blood vessel cannulation device which enables sensing a blood vessel at a first location, and correspondingly enables inserting a cannula adjacent the first location and in alignment along the blood vessel, and thus into the blood vessel.

It is another object of this invention to provide a blood vessel cannulation device which enables sensing the blood vessel, accounts for the orientation of the blood vessel by aligning the sensor location point or points with the cannula, and allows for the insertion of a cannula adjacent the sensed location.

It is a further object of this invention to provide a blood vessel cannulation device which enables sensing the location of a blood vessel through the use of multiple sensors with distinguishable outputs to allow for rapid and accurate location of the blood vessel, and accurate alignment of the sensors and cannula with the blood vessel.

SUMMARY OF THE DISCLOSURE

The invention is generally directed to blood vessel cannulation devices which assist in locating the blood vessel of a patient for cannulation, and which assure proper alignment of the canula over the blood vessel for precise insertion of the cannula. Preferred blood vessel cannulation devices of the invention account for normal blood vessel orientation, and curvature, thereby increasing the probability of accurate insertion of the cannula.

In preferred embodiments, a blood vessel cannulation device includes a mounting assembly for mounting the cannulation device proximate the skin of the patient in the vicinity of a blood vessel. The mounting assembly has a bottom. A rotating assembly is mounted for rotation with respect to the mounting assembly, on an axis transverse to the bottom of the mounting assembly. A guide housing is mounted for rotation with the rotating assembly, and for traverse across the rotating assembly. A first sensor guide extends through the guide housing, for inserting a sensor through the guide housing to a first end of the first sensor guide. A second cannula guide extends through the guide housing, for inserting a cannula through the guide housing to a second end of the second sensor guide. An optional third sensor guide extends through the guide housing, for inserting a sensor through the guide housing to a third end of the third sensor guide. The third end is aligned with the first and second ends. Such a cannulation device is effective for locating a blood vessel for cannulation by rotating the rotating assembly such that the first and second ends define a line aligned with the blood vessel, and traversing the guide housing across the rotating assembly until the sensor senses the blood vessel.

In general, the end of the cannula guide is aligned with the ends of the sensor guides. Preferably, the end of the cannula guide is between the ends of the sensor guides.

Preferably the sensor guides and the cannula guide are oriented at angles not perpendicular, and thus not normal with respect to the bottom of the mounting assembly.

A locating assembly can be mounted to the mounting assembly, and extend downwardly from the bottom of the mounting assembly, and thereby assist in locating the mounting assembly on the skin of the patient proximate the blood vessel.

The device may include a first, and optionally a second, sensor, in the respective sensor guides, for sensing a blood vessel. Preferred sensors are ultrasonic probes.

Where two sensors are used, the outputs from the two sensors are preferably processed electronically such that the output signal from the first sensor is distinguishable from the output signal from the second sensor. The outputs may, for example be processed to provide audible outputs, having first and second pitches audibly distinguishable from each other by the human ear. Similarly, the outputs may be processed to provide visual outputs, having third and fourth outputs visually distinguishable from each other.

Figure 1:
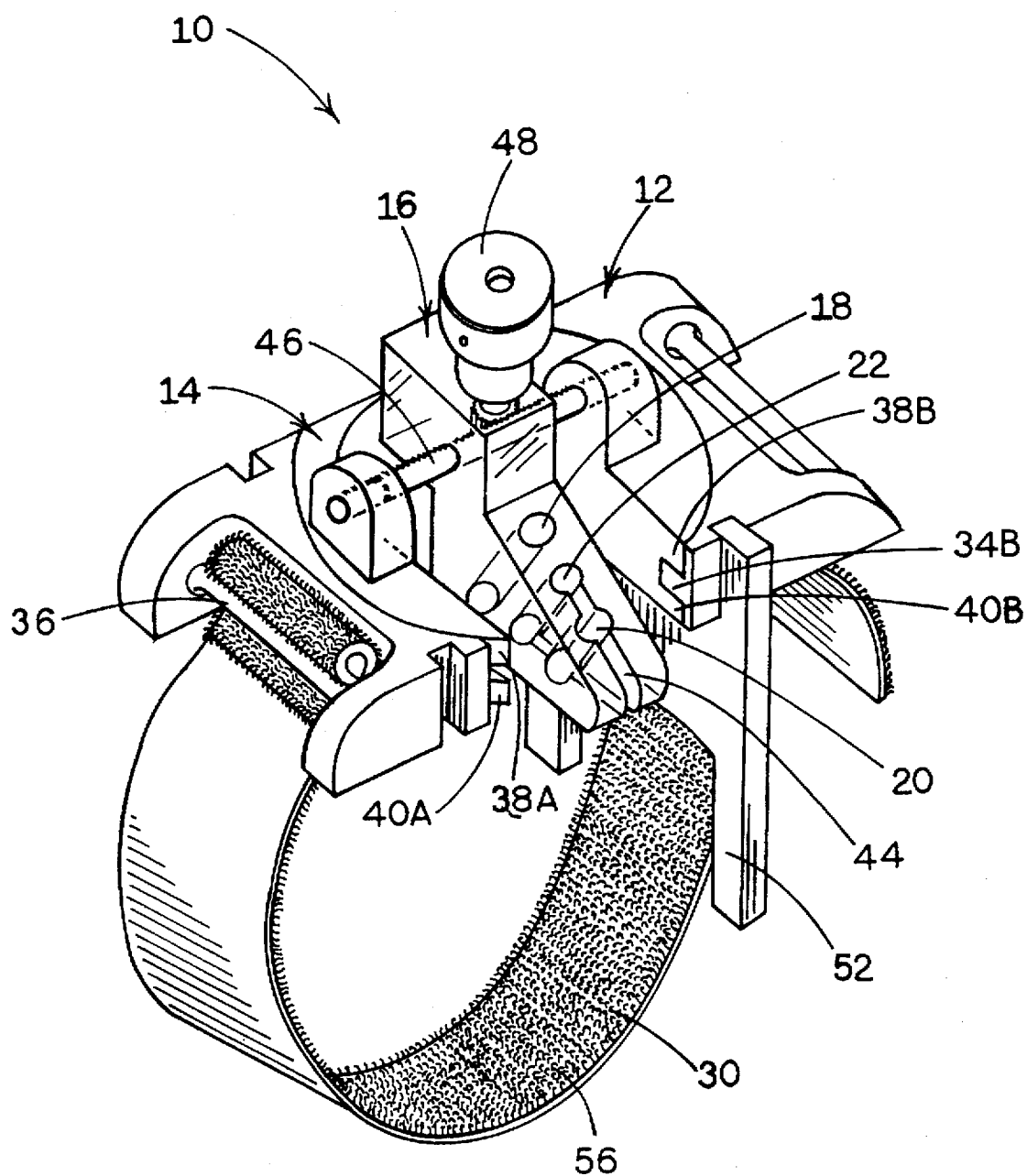
FIG. 1 shows a pictorial view of a blood vessel cannulation device of the invention.
Figure 2:
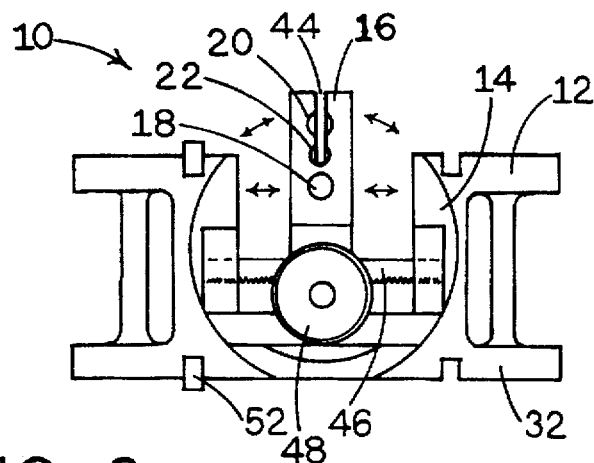
FIG. 2 shows a top view of the blood vessel cannulation device of FIG. 1.
Figure 3:
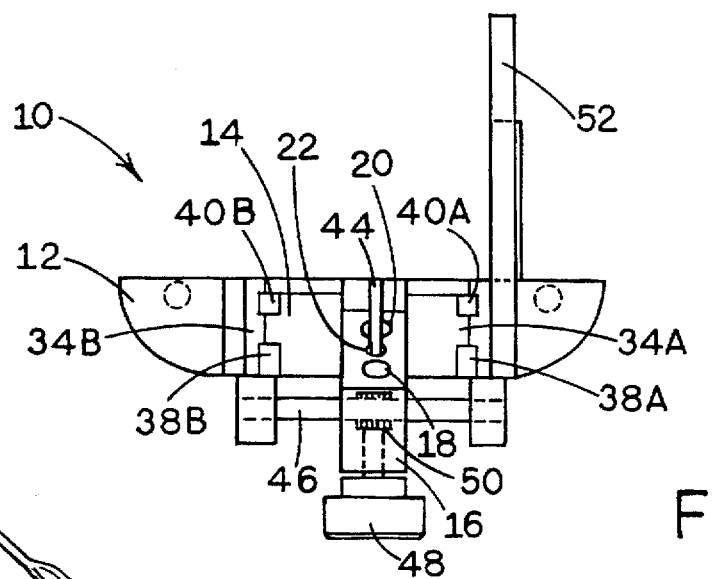
FIG. 3 shows a front view of the blood vessel cannulation device of FIG. 1 with the locating assembly mounted on the opposite side from that shown in FIG. 1.

It is to be understood that the invention is not limited in its application to the details of construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components.

DETAILED DESCRIPTION OF THE ILLUSTRATED EMBODIMENTS

Figure 4:
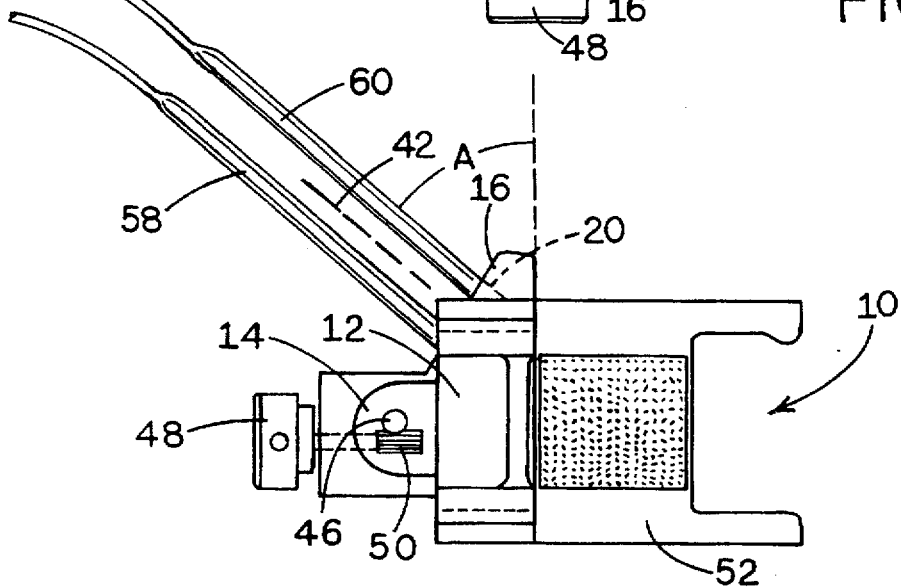
FIG. 4 shows a side view of the blood vessel cannulation device of FIG. 3, including first and second sensor probes.
Figure 5:
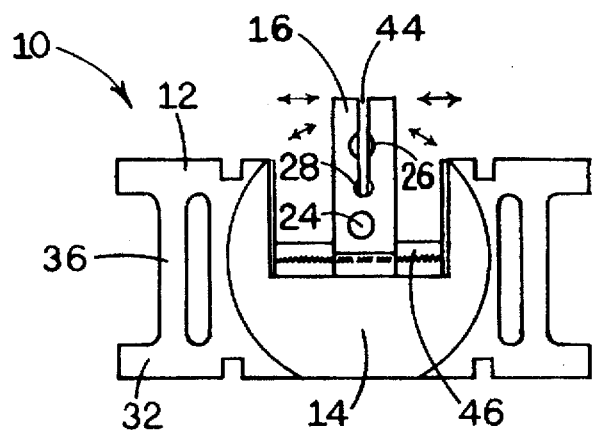
FIG. 5 shows a bottom view of the blood vessel cannulation device of FIG. 1, without the locating assembly.

Referring now by characters of reference to the drawings, and first to FIGS. 1 through 5, a blood cannulation device 10 of the invention is shown. The blood cannulation device comprises a mounting assembly 12. A rotating assembly 14 is mounted to the mounting assembly 12 for rotation in the directions shown by the arrows which extend from the perimeter of the rotating assembly in FIGS. 2 and 5. A guide housing 16 is mounted on, and rotates with, the rotating assembly 14, and is mounted for traverse across the rotating assembly 14 in the directions shown by the interiorly-disposed straight and aligned arrows in FIG. 2. Similar straight and aligned arrows are shown in FIG. 5.

The guide housing 16 includes sensor guides 18 and 20 and a cannula guide 22, all extending entirely through the guide housing 16 from a top surface of the guide housing to the bottom surface of the guide housing. The end 28 (FIG. 5) of the cannula guide is aligned with the bottom ends 24 and 26 of the respective sensor guides 18 and 20. Preferably, the cannula guide 22 is oriented at a non-perpendicular angle with respect to the bottom surface 32 of the mounting assembly 12.

A strap 30 is used to mount cannulation device 10 to a patient (e.g. on a wrist) thus to place the bottom surface 32 of the mounting assembly 12 securely on the skin of the patient proximate a blood vessel. In general, a first end of the strap is releasably mounted to mounting assembly 12 by an interference fit of a folded over portion 33 of the end of the strap between (i) the main body of mounting assembly 12 and (ii) a respective mounting rod 36. A rigid supporting stud, not shown, can, if desired, be mounted inside the folded over portion 33, to expand the thickness of the folded over portion for ensuring the interference fit.

Addressing a more detailed description of certain ones of the elements, and still referring to FIGS. 1 through 5, the mounting assembly 12 includes a ridge 34, indicated as 34A and 34B on its opposing ends. Ridge 34 extends about that portion of the outer perimeter of the rotating assembly which interfaces with the mounting assembly. Ridges 38, 40 extend about that interior portion of the mounting assembly which interfaces with the rotating assembly. Ridge 34 interfaces with ridges 38 and 40 on the rotating assembly 14, ridges 38 and 40 being indicated as 38A and 40A adjacent end 34A, and as 38B and 40B adjacent end 34B. The respective interfacing ridges 34, 38, and 40 mount the rotating assembly 14 to the mounting assembly 12 while allowing for rotation of the rotating assembly 14 with respect to the mounting assembly 12.

Guide housing 16 includes a slot 44. Slot 44 extends inwardly from a distal edge of the guide housing, and communicates with cannula guide 22 and sensor guide 20. In some embodiments, it is contemplated that slot 44 also extends inwardly to, and communicates with, sensor guide 18. As illustrated in the drawings, slot 44 preferably extends through the entire height of the guide housing, from the top of the guide housing to the bottom thereof. Slot 44 facilitates removal of the cannulation device 10 from the patient after a cannula has been inserted into the blood vessel, and while the cannula remains so inserted.

Other constructions of the guide housing are contemplated, including a multi-piece guide housing which can be disassembled, to facilitate removal of the cannulation device 10 from the patient after the cannula has been inserted into the blood vessel. An example of such multi-piece guide housing is shown in my U.S. Pat. No. 5,167,630, herein incorporated by reference in its entirety.

Rotating assembly 14 includes a rail 46 extending thereacross. A dial gear 50, attached to a positioning dial 48 on guide housing 14, interfaces with rail 46. Teeth on dial gear 50 cooperate with corresponding teeth on rail 46. Rotation of dial 48 causes corresponding rotation of dial gear 50 which causes guide housing 16 to traverse transversely back and forth along the rail 46, across the rotating assembly 14, the direction of traverse depending on the direction in which dial 48 is turned.

Figure 6A:
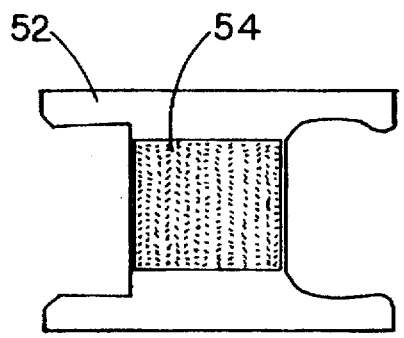
FIG. 6A shows a top view of the locating assembly.
Figure 6B:
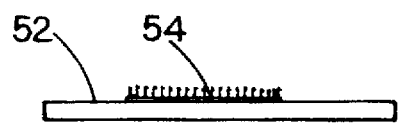
FIG. 6B shows a side view of the locating assembly.
Figure 7:
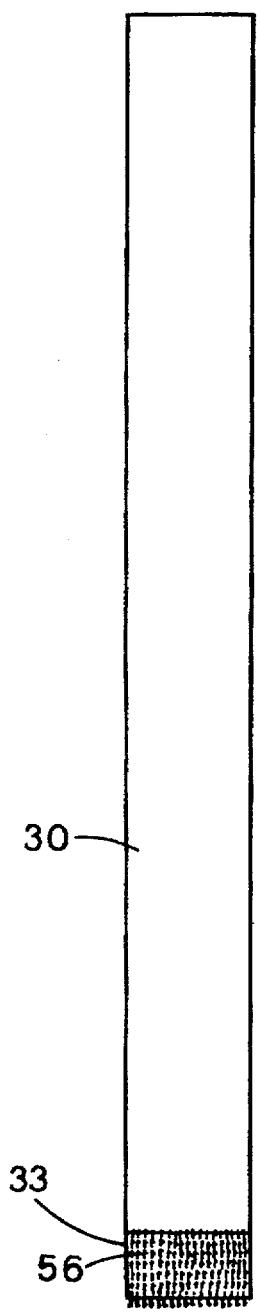
FIG. 7 shows a mounting strap used to mount the cannulation device of FIG. 1 to a patient.

A locating assembly 52, shown individually in FIGS. 6A and 6B, is attached to the mounting assembly 12 on either side thereof at respective slots shown in FIGS. 1, 2, 3, and 5, and extends downwardly with respect to bottom surface 32, as seen in FIGS. 1 through 4 to aid in locating the cannulation device 10 on the patient (e.g. at the patient's wrist). A first fastener 54 on the locating assembly 52 cooperates with a corresponding second fastener 56 on the mounting strap, thus releasably mounting the strap 30 to the locating assembly, and thereby releasably securing the cannulation device 10 to the patient. Fasteners 54 and 56 preferably have cooperating hooks and loops to provide the fastening means.

The cannulation device 10 is mounted to the wrist of a patient as follows. With the palm of the hand facing upwardly, and with the bottom surface 32 of the mounting assembly resting on the up-turned wrist, the locating assembly 52 is brought into abutment with the thumb side of the wrist. The locating assembly is thus normal to the skin of the patient which contacts the bottom surface 32 of the mounting assembly 12. With strap 30 releasably mounted to mounting assembly 12 at mounting rod 36, the strap is then placed around the wrist and secured to locating assembly 52 by fastening together cooperating (e.g. hook and loop) fasteners 54 and 56, thus temporarily, but securely mounting the cannulation device 10 to the wrist of the patient.

A sensor 58 (FIG. 4) is inserted into sensor guide 18 until the end of the sensor 58 is proximate the bottom end 24 of the sensor guide 18, and thus proximate the skin of the patient. A preferred sensor is an ultrasonic sensor. Where the sensor is an ultrasonic sensor, and in any such embodiments of the invention, suitable communication media, such as a gel, is preferably positioned between the end of the sensor 58 and the skin of the patient, to complete the communication path between a blood vessel and the sensor, and thus to facilitate sensing the blood vessel. The output of the sensor is useful for sensing the location of a blood vessel to be cannulated. Positioning dial 48 is turned, causing guide housing 16 to traverse across rotating assembly 14.

As guide housing 16 traverses across rotating assembly 14, the end of sensor 58 respectively traverses across the surface of the skin at the wrist of the patient. When the end of the sensor is positioned over a pulsating blood vessel such as an artery, the pulsating causes an output, from a preferred sensor, which varies with each pulsation. Thus, the variation in output from the sensor is an indication that the sensor is positioned over the blood vessel.

With the rotating member held in place, the sensor 58 is then removed from the sensor guide 18 and similarly inserted into the second sensor guide 20 until the end of the sensor 58 is proximate the bottom end 26 of the sensor guide 20, and thus proximate the skin of the patient. Rotating assembly 14 is then rotated with respect to the mounting assembly 12, and traversed across the mounting assembly, until the blood vessel is again sensed, while generally retaining the earlier location of the end 24 of the first sensor guide. The sensor 58 is then removed from the sensor guide 20 and alternately reinserted into sensor guides 18 and 20, making small adjustments to the lateral position of the guide housing 16, and the rotational position of rotating assembly 14, until the blood vessel can be sensed by sensor 58 in both of the sensor guides 18 and 20 without moving the guide housing 16.

When the blood vessel can be sensed in both sensor guides without moving the rotating assembly or the guide housing, the sensor ends 24, 26 are aligned with the blood vessel, and are positioned over the blood vessel. Similarly, since end 28 of cannula guide 22 is aligned with sensor ends 24, 26, the cannula end, too, is positioned over the blood vessel. With the cannula end 28 positioned over the blood vessel, a cannula is then inserted into the cannula guide 22 along path 42, as illustrated in FIG. 4, until the end of the cannula reaches the bottom end 28 of the cannula guide 22, the cannula thus being proximate the skin of the patient and aligned over the blood vessel. The cannula is then inserted into the blood vessel as desired to complete the cannulation. With the cannula inserted into the blood vessel, the function of the cannulation device is completed, and the cannulation device can be removed from the patient.

In removing the cannulation device, any sensor disposed in sensor guide 20 is removed, leaving slot 44 open and empty except for the cannula in cannula guide 22. Mounting strap 30 is released. Guide housing 16 is then removed from around the cannula, using slot 44 as the cannula exit path, but leaving the cannula substantially immobile as inserted in the blood vessel of the patient. Any sensor in sensor guide 18 is also preferably removed from the cannulation device before the cannulation device is removed from the patient.

In another embodiment, with sensor 58 in place in sensor guide 18, a second sensor 60 is inserted into sensor guide 20 until the end of the second sensor 60 is proximate the end 26 of the sensor guide 20, and thus proximate the skin of the patient. The process of traversing guide housing 16 and rotating assembly 14 is then completed with both sensors in place.

In this embodiment, the outputs of the respective sensors 58, 60 are preferably distinguishable from each other to allow for concurrent sensing of the blood vessel at both sensor guide ends 24, 26. For example, using two ultrasonic sensors 58, 60 concurrently, the output signals can be processed through conventional electronic ultrasonic processors which process ultrasonic signals, to create first and second audible outputs. The two ultrasonic processors can be adjusted, for example, to output two separate and distinct pitches, audibly distinguishable from each other by the human ear.

In other embodiments, the output signals may be processed for visual presentation such as on a cathode ray tube, wherein the two output signals are presented as visible representations of the signals visually distinguishable from each other by the human eye.

Whatever the output medium, the two representations can be presented in separate representational output devices, or in a single such output device having two output representations, one for each sensor.

In preferred embodiments, the sensor 58, or sensors 58 and 60 are ultrasonic probes. Preferably, the sensor guides 18, 20 are aligned at non-perpendicular angles "A" with respect to the bottom surface 32 of the mounting assembly 12. See FIG. 4. The guides 18, 20, and 22 can all be aligned with each other in a common plane as shown in, for example FIGS. 1–3 and 5. In the alternative, they may represent two or more intersecting planes (not shown). Such alignment of the planes is not critical. What is critical is that the end 28 of the cannula guide be aligned with ends 24, 26 of the sensor guides. End 28 is preferably located between ends 24, 26, but if not, should be sufficiently close to one of ends 24, 26 that the end 28 will be over the blood vessel when the sensor guides are over the blood vessel, in spite of any normal curvature of the paths of blood vessels, such as in the wrist.

Ultrasonic probes, as preferred herein, can, sense the blood when the length of the probe is oriented perpendicular to the blood vessel as taught in my U.S. Pat. No. 5,167,630. However, such ultrasonic probes use the location of blood vessel primarily by sensing change in flow velocity of blood elements such as the red blood cells, by a general application of the Doppler effect. Thus, any degree of alignment of the probe along the direction of flow of the blood in the vessel provides a desired increase in sensitivity of the probe to the flow of the blood, as compared to having the probe oriented perpendicular to the blood vessel. Sensitivity of the probe increases with increasing angle from the perpendicular to about 45 degrees, and then gradually diminishes as the angle is further increased from the perpendicular, until the signal is entirely lost at about 80 degrees. Thus, the probe can be oriented at any angle up to about 80 degrees from the perpendicular and be operable. However, the least preferred angle is a perpendicular angle because of the poor sensitivity of ultrasonic probes at that orientation.

Correspondingly, any angle "A" (FIG. 4) of about 10 degrees up to, but less than, 90 degrees is preferred. While 90 degrees is operable, it represents a substantial reduction, or trough, from peak sensitivity of the probe, and is thus not preferred. More preferred angles "A" are angles between about 20 degrees and about 85 degrees. Still more preferred angles are between about 25 degrees and about 80 degrees. Highly desirable angles are between about 30 degrees and about 70 degrees, where the output signal from ultrasonic sensors is particularly strong.

The angle "A" can be measured on either side of the perpendicular because blood flow can be detected whether flowing toward the face of the probe (at the bottom of the probe) or away from the face of the probe. Thus, as viewed in FIG. 4, angle "A" can be acute or obtuse, but is preferably not perpendicular.

As used in the claims that follow, an acute angle is any angle with respect to the bottom of the mounting assembly, except a perpendicular angle. Thus, where angle "A" as illustrated could be increased to be obtuse with respect to the base leg shown in FIG. 4, the complementary angle defined with respect to a base leg extending in the opposite direction is an acute angle. Where the claims specify acute angle, such complementary acute angles are included.

While not critical, it is preferred that angle "A" be defined within, or substantially within, a plane passing through the blood vessel and perpendicular to the skin of the patient. Such orientation utilizes existing skills of medical professionals wherein such orientation is preferred for orientation of the cannula.

In order to ensure that the cannulation device 10 is aligned with the blood vessel, the spacing between sensor guide ends 24, 26 should be sufficiently small to avoid misalignment due to normal curvature of the blood vessel between ends 24 and 26. Preferably, the spacing between sensor guide ends 24, 26 is less than about 1 inch. More preferably, the spacing between sensor guide ends 24, 26 is about 0.5 inch or less. To provide assurance that cannula guide end 28 will align with the blood vessel when the sensors are so aligned, cannula guide end 28 is preferably adjacent at least one of the sensor guide ends 24, 26, and is preferably between guide ends 24, 26.

In some embodiments of the invention, the guide housing 16 includes single sensor guide 18, and cannula guide 22. Sensor 58 is inserted into sensor guide 18 until the end of sensor 58 is proximate end 24 of sensor guide 18, and thus proximate the skin of the patient. Guide housing 16 is then made to traverse across rotating assembly 14, by turning positioning dial 48, until the blood vessel can be sensed by sensor 58. Rotating assembly 14 is rotated with respect to the mounting assembly 12 until sensor guide end 24 and cannula guide end 28 are generally aligned over the blood vessel. A cannula is then inserted into cannula guide 22 along path 42, as shown in FIG. 4, for venipuncture. In these embodiments, an especially short spacing is preferred between ends 24 and 28.

In still other embodiments of the invention, guide housing 16 is mounted directly to mounting assembly 12. Rotating assembly 14 is omitted. Thus, guide housing 16 traverses across rail 46 on mounting assembly 12. Guide housing 16 includes a single sensor guide 18 with optional second sensor guide 20, oriented at an angle "A" not perpendicular to the surface 32. End 24 of sensor guide 18 is adjacent end 28 of cannula guide 22. A sensor 58 is inserted into sensor guide 18 until the end of the sensor is proximate end 24 of sensor guide 18, and thus proximate the skin of the patient. The inventor herein has discovered that orientation of the sensor guide at a non-perpendicular angle "A" measured with respect to the bottom surface 32 of mounting assembly 12 increases the probability that the sensor will accurately sense the blood vessel. The guide housing 16 is made to traverse across the mounting assembly 12, by turning the positioning dial 48, until the blood vessel can be sensed by the sensor 58. Once the blood vessel has been sensed, a cannula is inserted into the cannula guide 22 along path 42, as shown in FIG. 4, for venipuncture.

While this embodiment is useful for locating blood vessels generally aligned with, for example, the length of a person's arm, rotation of the guide housing with respect to the mounting assembly is not contemplated, whereby blood vessels not aligned with the appendage to which the device is mounted may not be properly located. Accordingly, the embodiments including rotating assembly 14 are preferred.

In preferred embodiments, a blood vessel to be targeted for cannulation is first selected by selecting from those blood vessels which can be seen through the skin. Then the cannulation device 10 is mounted to the appendage (e.g. wrist) over the selected blood vessel, and on the surface of the skin. After the device is mounted to the appendage, rotating assembly 14 is rotated until the applicable guides 18, 20, and 22 are visually aligned with the selected vessel. Then one or more sensors 58, 60 are inserted in the sensor guides and connected to a appropriate output device, or devices. Communication gel is used at the ends of the sensors as appropriate. Dial 48 is then rotated to bring the ends 24 and/or 26 over the blood vessel, and to enable the sensor or sensors to thus sense the blood vessel. When the blood is sensed by a sensor at one of ends 24, 26, small adjustments are made to rotating assembly 14 and dial 48 to bring both ends 24 and 26 into position over the blood vessel, whereby the blood vessel can be sensed at both ends 24 and 26 without moving either rotating assembly 14 or guide housing 16. When the blood vessel can be sensed at both ends 24 and 26 without moving either the rotating assembly or the guide housing, both ends 24 and 26 are aligned over the blood vessel. Accordingly, end 28 of the cannula guide is also positioned over the blood vessel. The cannula can then be inserted through the cannula guide with assurance that the cannula will be properly inserted into the blood vessel.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

Having thus described the invention, what is claimed is:

1. A method of locating a blood vessel of a patient for cannulation, the method comprising the steps of:
    (a) sensing the blood vessel at a first location with a sensor;
    (b) sensing the blood vessel at a second location with said sensor, the blood vessel extending between the first and second locations;
    (c) placing a cannula proximate the blood vessel of the patient at a third location, for insertion into the blood vessel, the third location being proximate at least one of the first and second locations, and aligned with the first and second locations.

2. A method as in claim 1, the sensor comprising an ultrasonic probe.

3. A method of locating a blood vessel of a patient for cannulation, the method comprising the steps of:
    (a) sensing the blood vessel at a first location with a first sensor extending through a first sensor guide to a first end;
    (b) sensing the blood vessel at a second location with a second sensor extending through a second sensor guide to a second end;
    (c) placing a cannula proximate the blood vessel of the patient at a third location, for insertion into the blood vessel, the third location being proximate at least one of the first and second locations, and aligned with the first and second locations.

4. A method as in claim 3, the first sensor providing a first output signal, the second sensor providing a second output signal, and the first output signal being distinguishable from the second output signal, the method including the step prior to step (c) of,
    (d) concurrently sensing the blood vessel at both the first and second locations by concurrently observing sensing indications at both of the first and second output signals.

5. A method as in claim 3, the first and second output signals being audible, the pitch of the first output signal being audibly distinguishable by the human ear from the pitch of the second output signal, the method including the step, prior to step (c), of
    (d) concurrently sensing the blood vessel at both the first and second locations by concurrently observing sensing indications at both of the first and second output signals.

6. A method as in claim 3, the first and second output signals being visible, the first output signal being visually distinguishable, by the human eye, from the second output signal, the method including the step, prior to step, (c) of
    (d) concurrently sensing the blood vessel at both the first and second locations by, concurrently observing sensing indications at both of the first and second output signals.

7. A method as in claim 3, the first and second sensors comprising ultrasonic probes.

8. A method of locating a blood vessel of a patient for cannulation, the method comprising the steps of:

(a) placing proximate the skin of the patient in the vicinity of the blood vessel a cannulation device, the cannulation device comprising a mounting assembly for mounting the cannulation device to the patient, a rotating assembly mounted for rotation with respect to the mounting assembly, on an axis transverse to the skin of the patient to which the cannulation device is proximate, a guide housing mounted for rotation with the rotating assembly and for traverse across the rotating assembly, a first sensor guide extending through the guide housing to a first end of the first sensor guide proximate the skin of the patient, a second cannula guide extending through the guide housing for inserting a cannula through the guide housing to a second end of the second cannula guide proximate the skin of the patient;

(b) inserting a sensor into the first sensor guide to the first end proximate the skin of the patient; and (c) traversing the guide housing across the rotating assembly until the sensor senses the blood vessel.

9. A method as in claim 8, the method including the step of (d) rotating the rotating assembly such that the first and second ends define a line aligned with the blood vessel.

10. A method as in claim 8, the sensor comprising a first sensor, the cannulation device including a third sensor guide extending through the guide housing to a third end of the third sensor guide proximate the skin of the patient, the third end being aligned with the first and second ends, the second end of the second cannula guide being adjacent at least one of the first and third ends, the method including the steps of (d) inserting a second sensor into the third sensor guide to the third end proximate the skin of the patient;

(e) rotating the rotating assembly until the second sensor senses the blood vessel; and (f) repeating steps (c) through (e) until the blood vessel can be concurrently sensed by both of the first and second sensors, the first, second, and third ends all thus being aligned with each other and with the blood vessel, whereby locating the first and second sensors in locations to sense the blood vessel concurrently locates the cannula over the blood vessel.

11. A method as in claim 8, the cannulation device including a third sensor guide extending through the guide housing to a third end of the third sensor guide proximate the skin of the patient, the third end being aligned with the first and second ends, the second end of the second cannula guide being adjacent at least one of the first and third ends, the method including the steps of (d) removing the sensor from the first sensor guide and inserting the sensor into the third sensor guide to the third end;

(e) rotating the rotating assembly until the sensor senses the blood vessel; and (f) repeating steps (c) through (e) until the blood vessel can be sensed by the sensor in both of the first and third sensor guides without moving the guide housing, whereby the first, second, and third ends are aligned with each other and with the blood vessel.

12. A method as in claim 8, the sensor comprising an ultrasonic probe.

13. A method as in claim 10, the first and second sensors comprising ultrasonic probes.

14. A method of locating a blood vessel of a patient for cannulation, the method comprising the steps of:

(a) placing proximate the skin of a patient in the vicinity of a blood vessel a cannulation device, the cannulation device comprising a guide housing, a first sensor guide extending through the guide housing to a first end of the first sensor guide proximate the skin of the patient, a second sensor guide extending through the guide housing to a second end of the second sensor guide proximate the skin of the patient, a third cannula guide extending through the guide housing to a third end of the third cannula guide proximate the skin of the patient, for inserting a cannula through the guide housing, the third end being aligned with the first and second ends;

(b) inserting a first sensor into the first sensor guide to the first end proximate the skin of the patient; and (c) traversing the guide housing across the rotating assembly until the first sensor senses the blood vessel;

(d) inserting a second sensor into the second sensor guide to the second end proximate the skin of the patient;

(e) rotating the rotating assembly until the second sensor senses the blood vessel; and (f) repeating steps (c) through (e) until the blood vessel can be concurrently sensed by both of the first and second sensors, such that the first, second, and third ends are aligned with each other and with the blood vessel.

15. A method as in claim 14, the first and second sensors comprising ultrasonic probes.

16. A method of locating a blood vessel for cannulation, the method comprising the steps of:

(a) placing proximate the skin of a patient in the vicinity of the blood vessel a cannulation device, the cannulation device comprising a guide housing, a first sensor guide extending through the guide housing to a first end of the first sensor guide proximate the skin of the patient, a second sensor guide extending through the guide housing to a second end of the second sensor guide proximate the skin of the patient, a third cannula guide extending through the guide housing to a third end of the third cannula guide proximate the skin of the patient, for inserting a cannula through the guide housing, the third end being aligned with the first and second ends;

(b) inserting a sensor into the first sensor guide to the first end proximate the skin of the patient; and (c) traversing the guide housing across the rotating assembly until the sensor senses the blood vessel;

(d) removing the sensor from the first sensor guide and inserting the sensor into the second sensor guide to the second end proximate the skin of the patient;

(e) rotating the rotating assembly until the sensor senses the blood vessel; and (f) repeating steps (c) through (e) until the blood vessel can be sensed by the sensor in both of the first and second sensor guides without moving the guide housing, whereby the first, second, and third ends are aligned with each other and with the blood vessel.

* * * * *